US00PP29067P2

(12) United States Plant Patent
Bowyer

(10) Patent No.: US PP29,067 P2
(45) Date of Patent: Mar. 6, 2018

(54) ***HELICHRYSUM* PLANT NAMED 'RED JEWEL'**

(50) Latin Name: *Helichrysum×amorginum*
Varietal Denomination: Red Jewel

(71) Applicant: Brenda Marion Bowyer, Chaddesden (GB)

(72) Inventor: Brenda Marion Bowyer, Chaddesden (GB)

( * ) Notice: Subject to any disclaimer, the term of this patent is extended or adjusted under 35 U.S.C. 154(b) by 0 days.

(21) Appl. No.: 15/530,480

(22) Filed: Jan. 20, 2017

(51) Int. Cl.
*A01H 5/02* (2006.01)

(52) U.S. Cl.
USPC ..... Plt./359

(58) Field of Classification Search
USPC ..... Plt./359
CPC ..... A01H 5/025
See application file for complete search history.

*Primary Examiner* — Kent L Bell
(74) *Attorney, Agent, or Firm* — C. A. Whealy

(57) ABSTRACT

A new and distinct cultivar of *Helichrysum* plant named 'Red Jewel', characterized by its upright and mounding plant habit; moderately vigorous growth habit; freely branching growth habit, bushy growth form; numerous inflorescences positioned above and beyond the foliar plane; inflorescence buds that are dark red purple in color; inflorescences with showy dark red purple-colored involucral bracts; and good postproduction longevity and garden performance.

2 Drawing Sheets

Botanical designation: *Helichrysum×amorginum.*
Cultivar denomination: 'RED JEWEL'.

BACKGROUND OF THE INVENTION

The present invention relates to a new and distinct cultivar of *Helichrysum* plant, botanically known as *Helichrysum×amorginum* and hereinafter referred to by the name 'Red Jewel'.

The new *Helichrysum* plant is a product of a controlled breeding program conducted by the Inventor in Derby, Chaddesden, United Kingdom. The objective of the breeding program is to create new mounding *Helichrysum* plants with unique and longer-lasting attractive inflorescence color.

The new *Helichrysum* plant originated from a cross-pollination in March, 2005 in Derby, Chaddesden, United Kingdom, of *Helichrysum×amorginum* 'Blorub', disclosed in U.S. Plant patent application Ser. No. 11/177,992 (now abandoned), as the female, or seed, parent with an unnamed proprietary selection of *Helichrysum×amorginum*, not patented, as the male, or pollen, parent. The new *Helichrysum* plant was discovered and selected by the Inventor as a single flowering plant from within the progeny of the stated cross-pollination in a controlled environment in Derby, Chaddesden, United Kingdom in March, 2006.

Asexual reproduction of the new *Helichrysum* plant by vegetative cuttings in a controlled environment in Derby, Chaddesden, United Kingdom since July, 2006, has shown that the unique features of this new *Helichrysum* plant are stable and reproduced true to type in successive generations.

SUMMARY OF THE INVENTION

Plants of the new *Helichrysum* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Red Jewel'. These characteristics in combination distinguish 'Red Jewel' as a new and distinct *Helichrysum* plant:

1. Upright and mounding plant habit.
2. Moderately vigorous growth habit.
3. Freely branching growth habit, bushy growth form.
4. Numerous inflorescences positioned above and beyond the foliar plane.
5. Inflorescence buds that are dark red purple in color.
6. Inflorescences with showy dark red purple-colored involucral bracts.
7. Good postproduction longevity and garden performance.

Plants of the new *Helichrysum* differ primarily from plants of the female parent, 'Blorub', primarily in inflorescence bud and involucral bract color as plants of 'Blorub' have lighter-colored inflorescence buds and involucral bracts. In addition, inflorescences of the new *Helichrysum* are longer-lasting than inflorescences of 'Blorub'.

Plants of the new *Helichrysum* differ primarily from plants of the male parent selection primarily in involucral bract color as plants of the male parent selection have yellow-colored involucral bracts.

Plants of the new *Helichrysum* can also be compared to plants of the *Helichrysum×amorginum* 'Pink Sapphire', disclosed in U.S. Plant Pat. No. 20,476. In side-by-side comparisons, plants of the new *Helichrysum* differ primarily from plants of 'Pink Sapphire' in involucral bract color as plants of 'Pink Sapphire' have pink-colored involucral bracts.

Plants of the new *Helichrysum* can also be compared to plants of the *Helichrysum×amorgianum* 'Ember Glow', disclosed in U.S. Plant Pat. No. 23,600. In side-by-side comparisons, plants of the new *Helichrysum* differ primarily from plants of 'Ember Glow' in involucral bract color as plants of 'Ember Glow' have light red to orange red-colored involucral bracts.

BRIEF DESCRIPTION OF THE PHOTOGRAPHS

The accompanying colored photographs illustrate the overall appearance of the new *Helichrysum* plant showing the colors as true as it is reasonably possible to obtain in colored reproductions of this type. Colors in the photographs may differ slightly from the color values cited in the detailed botanical description which accurately describe the colors of the new *Helichrysum* plant.

The photograph on the first sheet is a side perspective view of a typical flowering plant of the female parent 'Blorub' (left) and a typical flowering plant of 'Red Jewel' (right) grown in an outdoor nursery.

The photograph at the top of the second sheet is a close-up view of a typical inflorescence of 'Red Jewel'.

The photograph at the bottom of the second sheet is a close-up view of the upper and lower surfaces of typical leaves of 'Red Jewel'.

DETAILED BOTANICAL DESCRIPTION

The aforementioned photographs and following observations, measurements and values describe plants grown during the summer in 5-liter containers in an outdoor nursery in Bressingham, Norfolk, United Kingdom and under commercial practices typical of *Helichrysum* production. During the production of the plants, day temperatures ranged from 6° C. to 30° C. and night temperatures ranged from −3° C. to 15° C. During the winter, plants were grown in a polyethylene-covered tunnel. Plants were two years old when the photographs and description were taken. In the following description, color references are made to The Royal Horticultural Society Colour Chart, 2001 Edition, except where general terms of ordinary dictionary significance are used.

Botanical classification: *Helichrysum×amorgianum* 'Red Jewel'.

Parentage:

*Female, or seed, parent.*—*Helichrysum×amorginum* 'Blorub', disclosed in U.S. Plant patent application Ser. No. 11/177,992 (now abandoned).

*Male, or pollen, parent.*—Unnamed selection of *Helichrysum×amorginum*, not patented.

Propagation:

*Type.*—By vegetative cuttings.

*Time to initiate roots.*—About 15 days at temperatures about 18° C. to 21° C.

*Time to produce a rooted young plant.*—About ten weeks at temperatures about 18° C. to 21° C.

*Root description.*—Thin, fibrous; color, close to 161B.

*Rooting habit.*—Freely branching; dense.

Plant description:

*Plant form and growth habit.*—Upright and mounding plant habit; moderately vigorous growth habit; freely branching growth habit and bushy plant form; moderate growth rate.

*Plant height.*—About 35 cm.

*Plant diameter or spread.*—About 40 cm.

*Lateral branches.*—Arrangement: Numerous lateral branches arising in a basal rosette. Length: About 20 cm to 26 cm. Diameter: About 5 mm. Internode length: About 1.5 cm. Strength: Strong. Aspect: Upright to pendulous. Texture: Densely pubescent, pannose; with development, woody. Color: Close to 189C; with development, color becoming closer to 161B.

Leaf description:

*Arrangement.*—Alternate, simple; sessile, amplexicaul.

*Length.*—About 4 cm to 6 cm.

*Width.*—About 1.5 cm.

*Shape.*—Lanceolate.

*Apex.*—Obtuse.

*Base.*—Acuminate.

*Margin.*—Entire.

*Texture, upper and lower surfaces.*—Pubescent.

*Venation pattern.*—Pinnate.

*Color.*—Developing leaves, upper surface: Close to 189B. Developing leaves, lower surface: Close to 189C. Fully developed leaves, upper surface: Close to 189C; venation, close to 189C. Fully developed leaves, lower surface: Close to 189D; venation, close to 189D.

Inflorescence description:

*Appearance and flowering habit.*—Composite inflorescence form; inflorescences arranged in terminal compound umbels; involucral bracts arranged acropetally in numerous whorls on the receptacle; inflorescences borne above and beyond the foliar plane; uniform and freely flowering habit with about 100 inflorescences developing per plant; inflorescences face mostly upright.

*Fragrance.*—None detected.

*Flowering season.*—Plants begin flowering about 215 days after planting; in the garden, plants flower continuously from March to May in the United Kingdom.

*Inflorescence longevity.*—Inflorescences are long-lasting and can be cut, dried and used as an ever-lasting without the color fading; inflorescences persistent; on the plants, inflorescences last about three months.

*Inflorescence buds.*—Height: About 1 cm. Diameter: About 5 mm. Shape: Orbicular. Color: Close to 59A.

*Inflorescence size.*—Umbel diameter: About 5 cm. Umbel height: About 5 cm. Single inflorescence diameter: About 1 cm. Single inflorescence height: About 1 cm. Receptacle diameter: About 1 mm. Receptacle height: About 5 mm. Receptacle color: Close to 189D.

*Ray florets.*—Ray florets have not been observed to develop on inflorescences of plants of the new *Helichrysum.*

*Disc florets.*—Quantity and arrangement: Numerous, massed at the center of the receptacle. Length: About 2 mm. Width: About 1 mm. Shape: Elongated tubular. Apex: Acute. Base: Cuneate. Texture: Smooth, glabrous, Color, immature: Apex: Close to 59A. Mid-section: Close to 59B. Base: Close to 59D. Color, mature: Apex: Close to 59A. Mid-section: Close to 59B. Base: Close to 59C.

*Involucral bracts (phyllaries).*—Quantity per inflorescence: Numerous, arranged in numerous whorls. Length: About 5 mm. Width: About 1 mm. Shape: Lanceolate. Apex: Acute. Base: Attenuate. Margin: Entire. Texture, upper and lower surfaces: Papery. Color: When opening, upper surface: Close to 59A. When opening, lower surface: Close to 59B. Fully opened, upper surface: Close to 59B; color becoming closer to 59C with development. Fully opened, lower surface: Close to 59C.

*Peduncles*.—Length: About 1 cm. Diameter: About 1.5 mm. Strength: Strong. Texture: Pubescent. Color: Close to 189C; color becoming closer to 161B with development.

*Pedicels*.—Length: About 8 mm. Diameter: About 1 mm. Strength: Strong. Texture: Pubescent. Color: Close to 189C; color becoming closer to 161B with development.

*Reproductive organs*.—Present on disc florets only. Androecium: Quantity per floret: Typically five. Anther length: About 1 mm. Anther shape: Cylindrical. Anther color: Close to 59C. Pollen amount: Sparse. Pollen color: Close to 23D. Gynoecium: Quantity per floret: One. Pistil length: About 2 mm. Style length: About 1.5 mm. Style color: Close to 23C. Stigma color: Close to 23C. Ovary color: Close to 149D.

*Seeds*.—Amount: Sparse. Size: Dust-like. Color: Close to 161D.

Pathogen & pest resistance: Plants of the new *Helichrysum* have been observed to be tolerant to Powdery Mildew (*Erysiphe cichoracearum*). Plants of the new *Helichrysum* not been observed to be resistant to pests and other pathogens common to *Helichrysum* plants.

Garden performance: Plants of the new *Helichrysum* have been observed to have good garden performance and to tolerate rain, wind and temperatures ranging from about −8° C. to about 30° C. Plants of the new *Helichrysum* are tolerant to USDA Hardiness Zone 8.

It is claimed:

1. A new and distinct *Helichrysum* plant named 'Red Jewel' as illustrated and described.

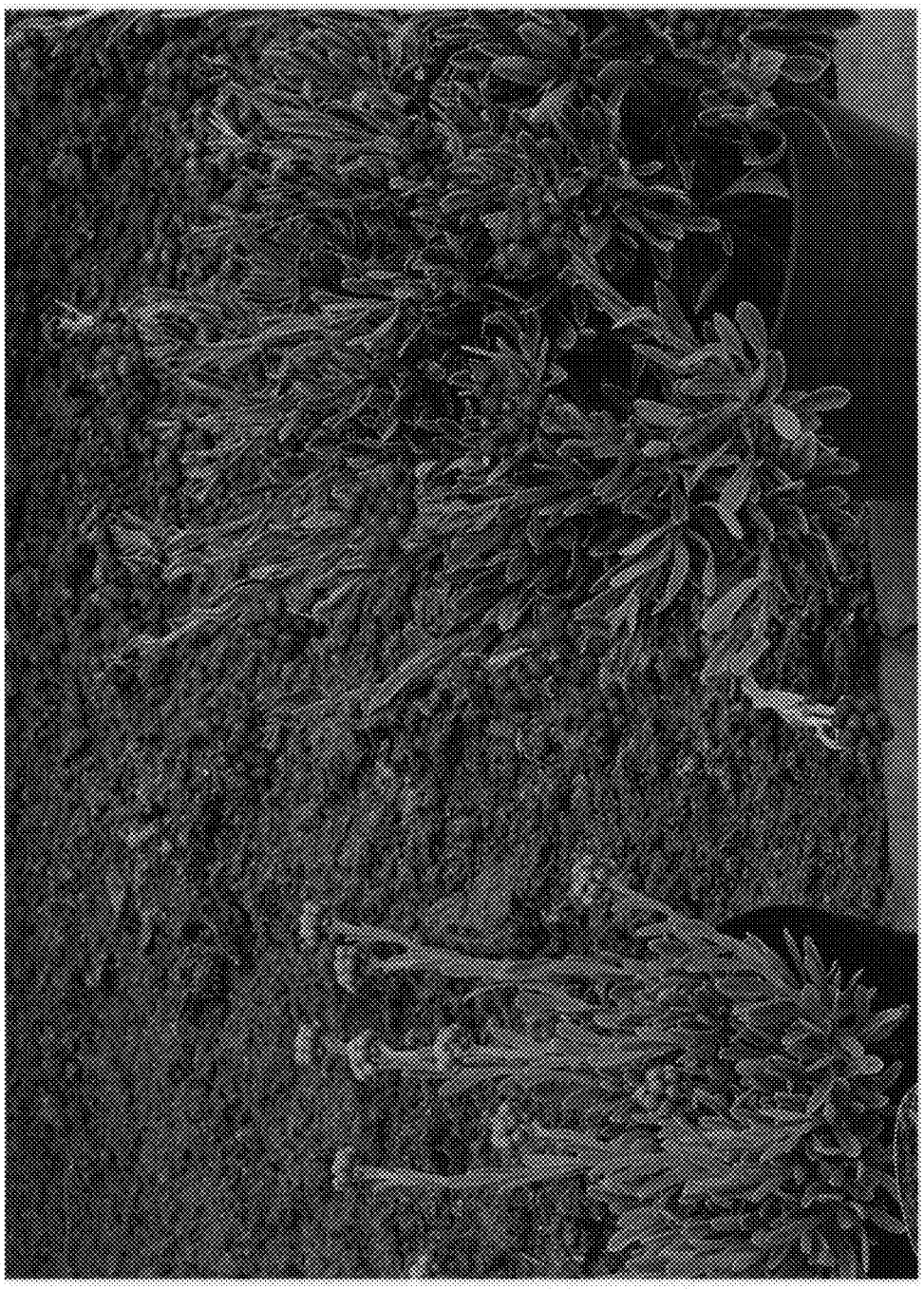

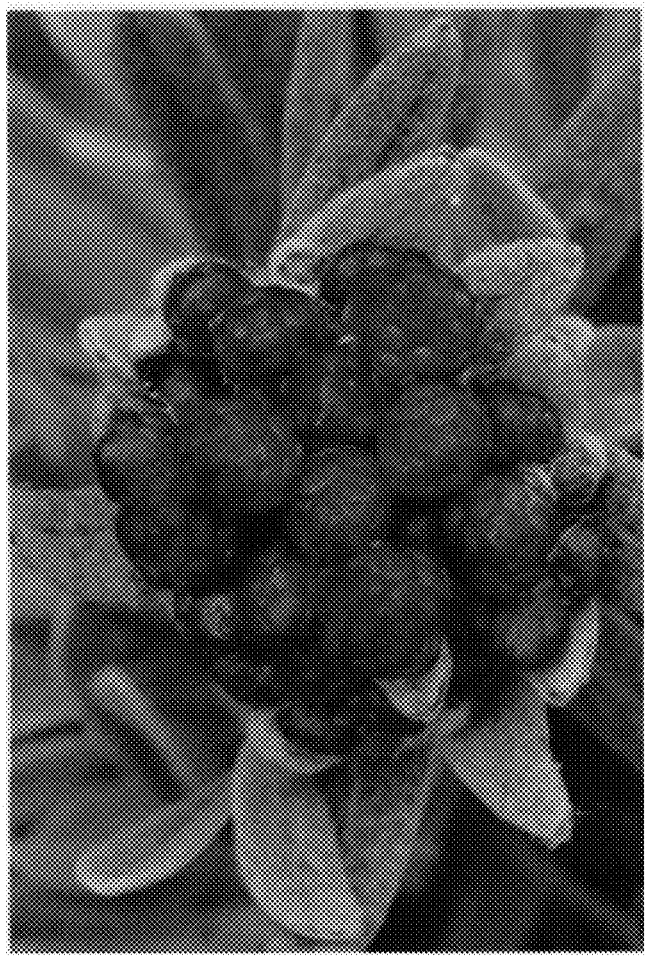
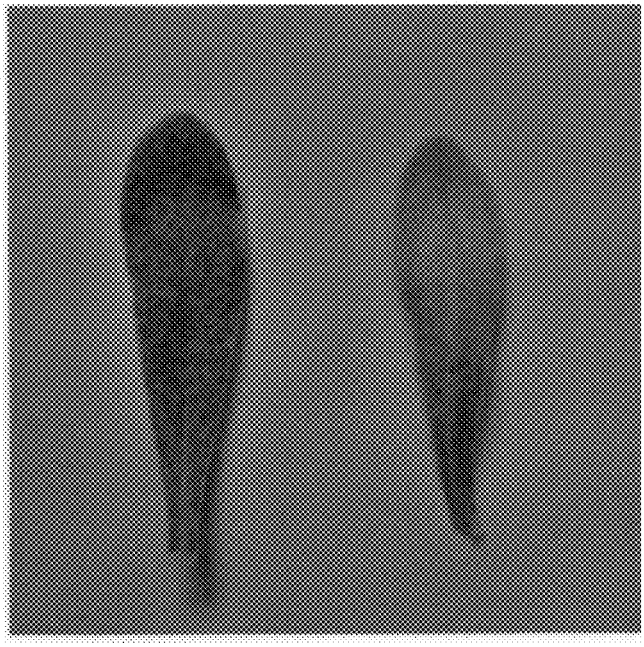

* * * * *